(12) United States Patent
Luke et al.

(10) Patent No.: US 8,846,964 B2
(45) Date of Patent: Sep. 30, 2014

(54) SYNTHETIC METHOD FOR PHOSPHAPLATIN COMPOUNDS

(71) Applicant: Phosplatin Therapeutics LLC, New York, NY (US)

(72) Inventors: Wayne D. Luke, West Lafayette, IN (US); Steffen Jost, Grundau (DE)

(73) Assignee: Phosplatin Therapeutics, New York, NY (US)

(*) Notice: Subject to any disclaimer, the term of this patent is extended or adjusted under 35 U.S.C. 154(b) by 0 days.

(21) Appl. No.: 14/032,704

(22) Filed: Sep. 20, 2013

(65) Prior Publication Data

US 2014/0024848 A1 Jan. 23, 2014

Related U.S. Application Data

(63) Continuation of application No. PCT/US2013/031885, filed on Mar. 15, 2013.

(60) Provisional application No. 61/651,200, filed on May 24, 2012.

(51) Int. Cl.
*C07F 15/00* (2006.01)

(52) U.S. Cl.
CPC .................. *C07F 15/0093* (2013.01)
USPC .......................................................... 556/17

(58) Field of Classification Search
CPC ................................................ C07F 15/0093
USPC ........................................................ 556/17
See application file for complete search history.

(56) References Cited

U.S. PATENT DOCUMENTS

| | | | | |
|---|---|---|---|---|
| 7,342,122 | B2* | 3/2008 | Odani | 556/17 |
| 7,700,649 | B2* | 4/2010 | Bose | 514/492 |
| 8,034,964 | B2 | 10/2011 | Bose | |
| 8,445,710 | B2* | 5/2013 | Bose | 556/17 |
| 8,653,132 | B2* | 2/2014 | Bose | 514/492 |
| 2009/0042838 | A1* | 2/2009 | Bose | 514/106 |
| 2009/0281319 | A1 | 11/2009 | Du Preez | |
| 2010/0233293 | A1* | 9/2010 | Bose | 424/649 |
| 2011/0313182 | A1* | 12/2011 | Bose | 556/17 |
| 2013/0064902 | A1* | 3/2013 | Bose | 424/649 |
| 2013/0165680 | A1* | 6/2013 | Bose et al. | 556/17 |
| 2013/0237503 | A1* | 9/2013 | Bose | 514/106 |

OTHER PUBLICATIONS

Moghaddas et al., Inorganica Chimica Acta, vol. 393, pp. 173-181 (2012).*
Mishur et al., Inorganic Chemistry, vol. 47, No. 18, pp. 7972-7982 (2008).*
Saouma, Synthetic Strategies to Improve the Cytotoxicity of Platinum-Based Cancer Therapeutics, Undergraduate Thesis, MIT, pp. 1-78, 2005. <<http://dspace.mit.ed u/bitstream/handle/1 721 . 1 /36279/77529534.pdf?sequence=1>>Last accessed May 1, 2013.

* cited by examiner

*Primary Examiner* — Porfirio Nazario Gonzalez
(74) *Attorney, Agent, or Firm* — Fox Rothschild LLP; Gerard P. Norton; Wansheng Jerry Liu

(57) ABSTRACT

This application discloses novel methods and processes for preparation and purification of phosphaplatin compounds. The improvements of the synthetic methods and purification processes include, but are not limited to, efficient and reproducible large-scale preparation of these useful pharmaceutical agents in high quality and good yield.

21 Claims, 2 Drawing Sheets

(A) am-2

(B) am-4

(C) en-2

(D) en-4

(E) dach-2

(F) dach-4

SYNTHETIC METHOD FOR PHOSPHAPLATIN COMPOUNDS

CROSS REFERENCE TO RELATED APPLICATIONS

This application is a U.S. Continuation Application of International Application No. PCT/US2013/031885, filed on Mar. 15, 2013, which claims the benefit under 35 U.S.C. §119(e) of U.S. Provisional Application No. 61/651,200, filed on May 24, 2012, both of which are incorporated herein by reference in their entirety.

FIELD OF THE INVENTION

This application relates to synthetic methods for preparation of phosphaplatin compounds, in particular monomeric platinum pyrophosphate compounds, useful as pharmaceutical agents, and processes for recrystallization and purification of these platinum pyrophosphate compounds.

BACKGROUND OF THE INVENTION

Platinum complexes, in particular diamine-based platinum complexes such as cisplatin, carboplatin, and oxaliplatin, are an important class of anti-cancer agents, which have been widely used for treating cancers such as ovarian, testicular, small cell lung, and colorectal cancers.

With the increasing cisplatin/carboplatin-resistance of cancers, for example, ovarian cancer, there have been efforts within industry to replace cisplatin/carboplatin with more effective, less-resistant chemotherapeutics, for example platinum oxalate, platinum phosphate and/or pyrophosphate complexes. However, not until recent years did platinum phosphate or pyrophosphate complexes gain importance in their potential as cancer-treating agents, partly because these complexes are prone to form insoluble phosphate-bridged dinuclear complexes. Although some dinuclear phosphato-platinum complexes were reported to possess excellent anti-cancer properties, further exploration of their applications as well as their syntheses were limited because of the poor solubility of these complexes in aqueous solutions. Although certain monomeric pyro- and triphosphate platinum complexes were known in the art, they were not suitable for pharmaceutical compositions because they would undergo phosphate hydrolysis in moderately acidic solutions to become insoluble dinuclear products (see Bose et al., *Inorg. Chem.*, 1985, 24, 3989-3996; and U.S. Pat. No. 7,342,122 and WO 2005/000858 to Odani et al., which are hereby incorporated by reference).

U.S. Pat. Nos. 7,700,649 and 8,034,964 (both to Bose), which are both incorporated by reference (the "Bose patents"), disclose synthetic routes and treatment methods involving a new class of platinum complexes, namely monomeric amine or diamine platinum pyrophosphate complexes. Among the pyrophosphato-platinum complexes disclosed in Bose patents are the amine or diamine platinum pyrophosphate complexes shown in FIG. 1. These complexes were found efficacious in the treatment of various cancers, including cisplatin and carboplatin-resistant cancers. However, until the present invention, syntheses of these compounds remained inefficient, and a process suitable for large-scale preparation of these complexes has not been reported. Various factors, for example, the sensitivity of the monomeric complexes to synthetic conditions, and their tendency to form dinuclear counterparts under certain conditions, make large-scale preparation and purification of these monomeric complexes a challenge.

SUMMARY OF THE INVENTION

The present application discloses an invention to meet the foregoing challenge.

In one aspect the present invention provides a new method for preparation of phosphaplatin compounds suitable for large-scale preparation. The new method overcomes a number of technological challenges and enables synthesis and isolation of monomeric complexes in multi-gram, multi-kilogram or larger scales.

In one embodiment, the new method uses a water miscible solvent as wetting agent, which enables the reaction to be run at a concentration 45-50 fold higher than that used in the existing processes. In another embodiment, the reaction is run at a higher temperature (preferably 60° C. versus 40° C. as used in the Bose patents). In another embodiment, treatment of the reaction mixture with a decolorizing and flocculating agent (preferably activated carbon) to remove minor colored impurities and other undissolved components allows for the removal of insoluble excess pyrophosphate salts prior to product isolation, and hence eliminates the limitation on the upper end of concentration of the reaction. Such a limitation is encountered in the literature due to precipitation of pyrophosphoric acid and/or its salts. In another embodiment of the present invention, cooling of the reaction mixture prior to pH adjustment in the crystallization step retards product decomposition. In another embodiment of the present invention, use of a more concentrated acid (for example, 2N instead of 1N nitric acid) for product precipitation allows for faster acid addition, thus reducing the time during which the compounds are exposed to the acid environment, and with it, reducing the acid-related impurities that result. This higher acid concentration also reduces dilution of the reaction mixture during the product precipitation step, and hence reduces loss of product into the reaction mother liquor.

In another aspect, the present invention provides a new method of recrystallizing and purifying monomeric amine or diamine platinum pyrophosphate complexes. The new method provides the platinum complexes as crystalline solids in high quality and good recovery yield, which makes it possible to study the properties of the complexes, including but not limited to their therapeutic effects, in a precise and quantitative manner.

In another aspect, the present invention provides a method of producing monomeric amine or diamine platinum pyrophosphate complexes or analogs in a "one-drop" and/or "one-pot" process in high quality and good isolated yield without further purification steps. The process has been successfully implemented to produce the (R,R)-DACH-2 product in 98.4% (w/w) purity without needing a further purification step at a scale that is 1,000-fold or more larger than that reported previously.

In another aspect, the present invention also provides a monomeric platinum pyrophosphate complex prepared or purified according to any of the embodiments described herein. The new synthetic methods and crystallization/recrystallization processes disclosed herein overcome many issues associated with the processes reported previously and provide many advantages over the existing processes. Notably, the methods disclosed herein are especially suitable for reproducible, commercial-scale manufacture of platinum complexes in high quality and good yields. These and other aspects of the present invention will be better appreciated by reference to the following drawing, detailed description and claims.

DETAILED DESCRIPTION OF THE INVENTION

Figure 1:
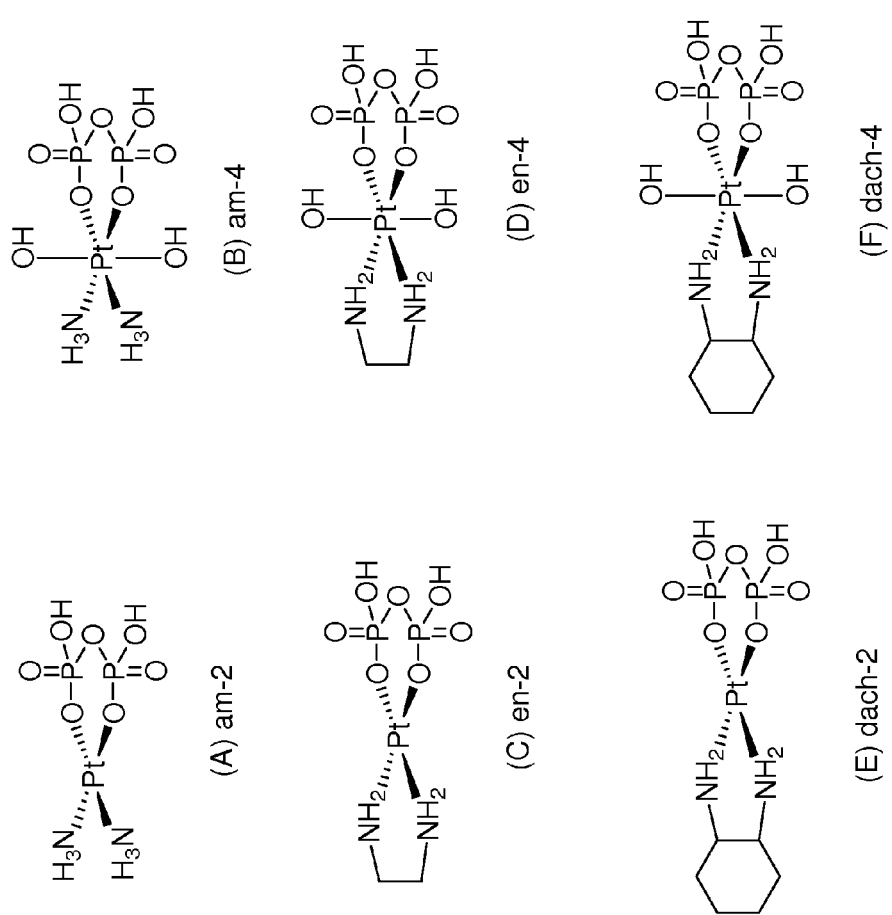
FIG. 1 shows the structures of several important platinum pyrophosphate complexes useful as anticancer agents disclosed in the Bose patents. (A) cis-diamine-(dihydrogen pyrophosphato)platinum(II) ("am-2"); (B) cis-diamine-trans-dihydroxo(dihydrogen pyrophosphato)platinum(IV) ("am-4"); (C) 1,2-ethanediamine-(dihydrogen pyrophosphato)platinum(II) ("en-2"); (D) 1,2-ethanediamine-trans-dihydroxo(dihydrogen pyrophosphato)platinum(IV) ("en-4"); (E) 1,2-cyclohexanediamine-(dihydrogen pyrophosphato)platinum(II) ("dach-2"); and (F) 1,2-cyclohexanediamine-trans-dihydroxo(dihydrogen pyrophosphato) platinum (IV) ("dach-4").

Synthesis and isolation of monomeric diamine (pyrophosphato) platinum(II) complexes are challenging because they can readily undergo reactions to form the corresponding dinuclear platinum complexes (see U.S. Pat. No. 4,234,500 and WO 2009/021082). For example, in the presence of DACH-Pt—Cl$_2$ or DACH-Pt—(OH$_2$)$_2$, (R,R)-DACH-2 could undergo reactions to form the corresponding undesired dinuclear platinum complex, or the "dimer" [{Pt(C$_6$H$_{14}$N$_2$)}$_2$P$_2$O$_7$] depicted below:

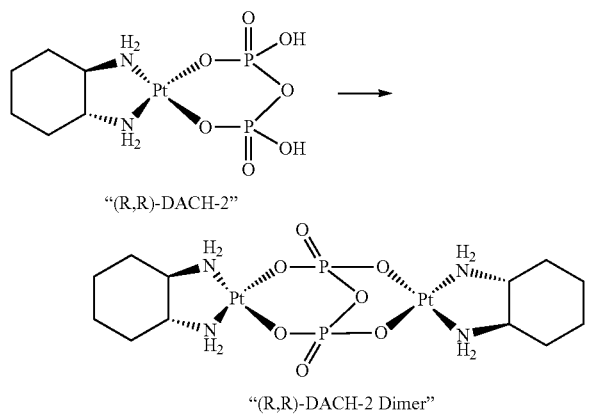

"(R,R)-DACH-2"

"(R,R)-DACH-2 Dimer"

The rate of (R,R)-DACH-2 aquation increases with decreasing pH. Thus at low pH, some (R,R)-DACH-2 hydrolyzes to form the aquated compound DACH-Pt—(OH$_2$)$_2$, which then reacts with (R,R)-DACH-2 in solution to form the dimer. The present invention overcomes this challenge.

In the following passages, the inventors of the present invention will disclose how this challenge has been overcome, while discussing how the other issues related to the existing processes have been resolved. In this disclosure, cyclohexanediamine (pyrophosphato)platinum (II) ("dach-2") is used as an illustrative example, which has three stereoisomers, i.e., the cis-isomer "cis-dach-2" and two enantiomers of trans-products "(R,R)-dach-2" and "(S,S)-dach-2", wherein "trans-", "cis-", "(R,R)-", and "(S,S)-" refer to the configurations of the two amino groups on the 1,2-cyclohexanediamine (i.e., 1,2-diaminocyclohexane, or "DACH") ligand, as known to a person skilled in the art. In particular, in this disclosure, the complex named "(R,R)-DACH-2" by the applicant refers to the "(R,R)-dach-2" enantiomer. These complexes may also be called by other similar names that will be understood by a person skilled in the art. Although only (R,R)-DACH-2 is used as an illustrative example, the invention should be equally applicable to other platinum pyrophosphate complexes of similar structures, which include, but are not limited to, those disclosed in the Bose patents, as will be understood by a person skilled in the art.

In one aspect, the present invention provides a method of preparing a monomeric platinum pyrophosphate complex, the method comprising the steps of: mixing a platinum dihalide compound with a pyrophosphate salt in a solvent system comprising water and a wetting agent, wherein the platinum dihalide compound and the pyrophosphate salt can undergo a reaction to form the desired monomeric platinum pyrophosphate complex; precipitating (crystallizing) the monomeric platinum pyrophosphate complex from the reaction mixture; and isolating the monomeric platinum complex from the reaction mixture. While preferable, it is not necessary to add a wetting agent to effect the reaction under the more concentrated reaction conditions in this invention. The product can be isolated by filtration or centrifugation, or any other methods as known to those skilled in the art. The isolated product is washed by water and/or an organic solvent, such as lower alkyl alcohol, in particular, methanol, ethanol, or isopropanol.

In one embodiment, the method further includes adjusting pH of the reaction mixture to below about 2 and cooling the reaction mixture to below room temperature prior to isolating the monomeric platinum (II) pyrophosphate complex.

In another embodiment, although generally not necessary in this invention, the method may further include concentrating the reaction mixture by distilling out a portion of solvent(s) prior to said precipitating (crystallizing).

In another embodiment, pH is adjusted by adding to the reaction mixture a required amount of a mineral acid. In some embodiments, the reaction mixture may be advantageously added into an acid to more rapidly lower the pH. The mineral acid is preferably nitric acid at a concentration of from about 1N to about 2N, preferably about 2N. Without being bound by any particular theory, advantages of the process using a more concentrated nitric acid include allowing faster addition of acid, thus reducing the time during which the compounds are exposed to the acid environment, and with it, reducing the acid-related impurities that result. This higher acid concentration also reduces dilution of the reaction mixture during the product precipitation step, and hence reduces loss of product into the reaction mother liquor. Based on the present disclosure, a person skilled in the art would be able to make adjustment to the choice of acid and/or its concentration in order to obtain optimum result. For example, a concentrated nitric acid may be used to adjust pH during crystallization, especially in the early stage, but a more diluted concentration, such as 2N and/or 1N, may be preferable for other reasons, such as safety, viscosity or heat control due to heat of mixing issues, and for fine tuning of the final pH.

In another embodiment, the wetting agent used for the reaction is a water miscible organic solvent.

In another embodiment, the wetting agent used for the reaction is a lower alkyl alcohol, preferably C$_1$-C$_4$ alkyl alcohol, more preferably methanol.

In another embodiment, the reaction is conducted at an elevated temperature. For illustration purpose, while not being so limited, the reaction for preparation of (R,R)-DACH-2 can be run at a temperature in the range between 30-70° C., or preferably between 45-65° C. In pure water the reaction may be run at even higher temperatures, which would result in a shorter reaction time. With the addition of an alcoholic wetting agent, in some embodiments, it may be preferable to run the reaction at reflux, which will allow the fastest reaction kinetics and ease of operational control in large, in particular commercial-scale, operations. As a person skilled in the art would understand, the preferred temperature depends on stability of the substrate and the product to be prepared. Any reasonable variation in this aspect would be within the scope of the present invention.

In another embodiment, sometimes preferably, the platinum dihalide compound is at a concentration so that at least about 65% of platinum precipitates out as the monomeric platinum pyrophosphate complex directly from the reaction mixture upon adjusting pH of the reaction mixture to about or below 2 at a temperature of about or below 20° C.

In another embodiment, sometimes more preferably, the platinum dihalide compound is at a concentration so that about 75-85% of platinum precipitates out as the monomeric platinum pyrophosphate complex directly from the reaction mixture upon adjusting pH of the reaction mixture to about or below 2 at a temperature of about or below 20° C.

Based on the present disclosure, those skilled in the art would be able to optimize the reaction and crystallization conditions to obtain a monomeric platinum pyrophosphate complex, in particular those specifically disclosed herein, in a desired yield and acceptable quality, depending on specific requirements, by balancing the parameters, such as concentration of reactants, and crystallization pH, temperature, and time, etc.

In another embodiment, the reaction is conducted at a concentration of the platinum dihalide compound such that further concentration of the solvent is not needed, or is minimally needed, for isolation of the product. Preferred concentrations of a reaction would depend on the solubility of the reagents and the product to be prepared, which would also depend on the ratio between water and the organic wetting agents, as a person skilled in the art would understand. Therefore, any reasonable variation and concentrations used for preparation of a specific similar product to (R,R)-DACH-2, would be within the scope of the present invention.

In another embodiment, the method further includes adding a decolorizing agent and filtering the decolorizing agent along with other undissolved components prior to the precipitating or crystallizing step. Any decolorizing agents known in the art would be suitable for this invention so long as they are inert and stable under the reaction conditions. One preferred example of such decolorizing agent is activated carbon.

In another embodiment, the monomeric platinum pyrophosphate complex contains two amine ligands independently selected from $NH_3$, substituted or unsubstituted aliphatic amines, and substituted or unsubstituted aromatic amines.

In another embodiment, the monomeric platinum pyrophosphate complex contains a diamine ligand.

In another embodiment, the diamine ligand is selected from substituted or unsubstituted aliphatic 1,2-diamines and substituted or unsubstituted aromatic 1,2-diamines.

In a preferred embodiment, the diamine ligand is an aliphatic 1,2-diamine selected from 1,2-ethylene-diamine and cyclohexane-1,2-diamine.

In another aspect, the present invention provides a method of purifying a monomeric platinum pyrophosphate complex, comprising dissolving the monomeric platinum pyrophosphate complex in a buffer and precipitating (crystallizing) the complex from the buffer.

In one embodiment, the buffer is a bicarbonate buffer having a pH in the range of 6-9.

In another embodiment, the method of purification further includes the steps of heating the monomeric platinum pyrophosphate complex until it is dissolved, treating the solution with a decolorizing agent, filtering the solution to remove the decolorizing agent and other undissolved components, and cooling the filtrate to crystallize the complex.

In another embodiment, the decolorizing agent is activated carbon.

In another embodiment, the buffer solution further contains a pyrophosphate salt.

In another embodiment, the monomeric platinum pyrophosphate complex contains two amine ligands independently selected from $NH_3$, substituted or unsubstituted aliphatic amines, and substituted or unsubstituted aromatic amines.

In another embodiment, the monomeric platinum pyrophosphate complex contains a diamine ligand.

In another embodiment, the diamine ligand is selected from substituted or unsubstituted aliphatic 1,2-diamines and substituted or unsubstituted aromatic 1,2-diamines.

In a preferred embodiment, the diamine ligand is an aliphatic 1,2-diamine selected from 1,2-ethylene-diamine and cyclohexane-1,2-diamine.

In another preferred embodiment according to any of the methods described above, the pyrophosphato-platinum (II) complex has a formula of (I) or (II):

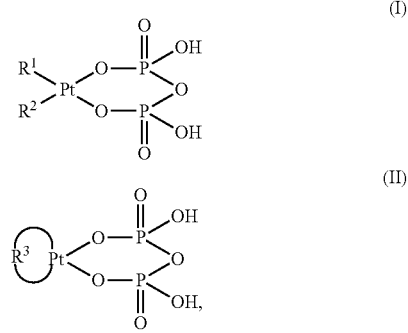

or a salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic or aromatic 1,2-diamines.

In another preferred embodiment, $R^1$ and $R^2$ in formula (I) are each independently selected from $NH_3$, methyl amine, ethyl amine, propyl amine, isopropyl amine, butyl amine, cyclohexane amine, aniline, pyridine, and substituted pyridine; and $R^3$ in formula (II) is selected from ethylenediamine and cyclohexanediamine.

In a more preferred embodiment, wherein the platinum complex (II) is selected from:

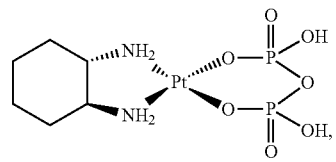

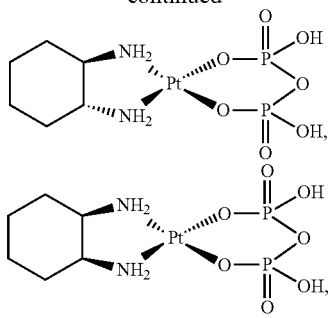

and salts and mixtures thereof.

In another aspect, the present invention provides a method of producing monomeric amine or diamine platinum pyrophosphate complexes in high quality and good isolated yield in a "one drop" process. In one embodiment, the method comprises the steps of (a) reacting an amine or diamine platinum halide complex with an inorganic pyrophosphate salt in an aqueous solution; (b) treating the reaction mixture with activated carbon; (c) removing the activated carbon and other solid impurities formed during the reaction by filtration; and (c) acidifying the filtrate solution to precipitate out the platinum complexes. Depending on the reaction conditions and control and the purpose of a desired product, the "one drop" process can produce the desired product in sufficient quality without needing a further purification, such as recrystallization, step.

In another embodiment, sometimes preferably, the activated carbon is not added directly into the reaction mixture, but used in a different manner or replaced entirely by an equivalent technique. For example, it could be replaced by an inline filter cartridge containing a filter medium, such as an activated carbon-containing filter pad, which would simplify operations, in particular the cleaning process for the reactor, in addition to providing other advantages.

In another embodiment, sometimes preferably, the reaction mixture is passed through an inline filter cartridge containing a filtration medium, such as an activated carbon-containing filter pad, to a second clean vessel so that undesired solid and impurities formed during the reaction are captured in the filter cartridge, and the filtered reaction mixture can be acidified in the second clean tank to give the desired product. This filtration process can be implemented through pressurizing the reactor or using a pump, or by any other technique known to a person skilled in the art.

In another embodiment, sometimes preferably, the reaction mixture is forced to pass through an inline filter cartridge containing a filtration medium, such as an activated carbon-containing filter pad through a pump, and the filtrate solution is circulated back to the reaction vessel. Upon circulating for a predetermined volume of liquid, when the undesired solids and impurities formed during the reaction are essentially removed by the filter cartridge, the filtered reaction mixture is acidified in the reaction vessel to give the desired product. This mode of operation has the advantage of using the same reaction vessel to produce the desired product in a "one-pot" process, thus simplifying the operations and saving costs associated with use of a second vessel.

As a person of ordinary skill in the art would understand, as in any other synthetic methods and processes, the product quality produced from a particular reaction or process batch could be affected by a number of conditions, for example, quality of reactants and reaction conditions and control.

When any of the "one-drop" and/or "one-pot" processes described herein produces a desired product that does not meet the quality specifications for a particular purpose, such product obtained can be further purified by the recrystallization processes as described herein.

Therefore, in another embodiment, sometimes preferably, the processes according to any embodiments as described herein further comprise a recrystallization step to purify the crude product obtained. Such recrystallization step would not only serve to purify the product obtained, but may also serve to obtain the final product in a particular crystalline form, including but not limited to desired polymorph(s), and/or of a particular desired particle size range or distribution. Such and any other related processes will be well within the knowledge of a person of ordinary skill in the art, and thus any variants thereof are all encompassed by the present disclosure.

In another aspect, the present invention provides monomeric platinum pyrophosphate complexes prepared or purified according to any of the embodiments described above. To our knowledge, the present invention for the first time provides reproducible methods to obtain this type of monomeric phosphaplatin compounds, with (R,R)-DACH-2 as an illustrative example, in high-quality crystalline form and good yield, at a scale that allows for use of the compounds in pre-clinical and clinical investigation. These phosphaplatin compounds are useful drug candidates for treating a variety of cancers, including colorectal and lung cancers, and in particular cisplatin-resistant ovarian cancer.

In another aspect, the present invention provides a method of preparing a monomeric platinum (IV) pyrophosphate complex, or a salt thereof, comprising: (1) preparing a monomeric platinum (II) pyrophosphate complex according to any of the embodiments disclosed herein; (2) oxidizing the monomeric platinum (II) pyrophosphate complex prepared in (1) with an oxidant, such as hydrogen peroxide; and (3) isolating the monomeric platinum (IV) pyrophosphate complex.

In one embodiment, the monomeric platinum (IV) pyrophosphate complex has a formula (III) or (IV):

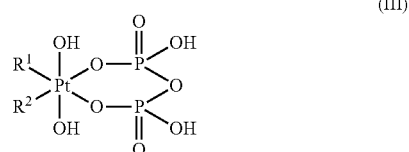

(III)

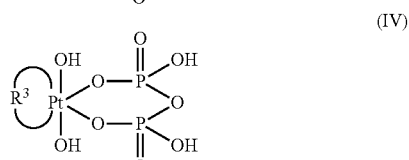

(IV)

or a salt thereof, wherein R1 and R2 are each independently selected from $NH_3$, substituted or unsubstituted aliphatic amines, and substituted or unsubstituted aromatic amines; and wherein R3 is selected from substituted or unsubstituted aliphatic diamines, and substituted or unsubstituted aromatic diamines.

In a preferred embodiment, the monomeric platinum (IV) pyrophosphate complex has a formula (IV), wherein $R^3$ is 1,2-ethylene-diamine ("en-4") or cyclohexane-1,2-diamine ("dach-4").

In another aspect, the present invention provides the monomeric platinum (II) or (IV) pyrophosphate complex prepared or purified by a method according to any of the embodiments described, or a pharmaceutically acceptable salt thereof, having a purity of at least 96.0% (w/w) or at least 98.0% (w/w).

In another aspect, the present invention provides the monomeric platinum (II) or (IV) pyrophosphate complex prepared or purified by a method according to any of the embodiments described, or a pharmaceutically acceptable salt thereof, for use in the treatment of a cancer that is resistant to one or more anticancer agents selected from cisplatin, carboplatin, and oxaliplatin.

In another aspect, the present invention provides a composition comprising a monomeric platinum (II) or (IV) pyrophosphate complex prepared or purified by a method according to any of the embodiments described, or a pharmaceutically acceptable salt thereof, and a pharmaceutically acceptable carrier, for use in the treatment of a cancer that is resistant to one or more anticancer agents selected from cisplatin, carboplatin, and oxaliplatin.

In a preferred embodiment, the drug resistant cancer is selected from ovarian, testicular, small cell lung, and head and neck cancers. The new synthetic method and recrystallization processes disclosed herein overcome many issues associated with the processes reported previously and provide many advantages over the existing processes. For example, first, it increases the reaction concentration by a factor of 45-50 fold and increases the reaction temperature from about 40° C. to about 60° C., which improves the efficiency of the reaction. Second, addition of a water miscible organic solvent to the reaction mixture improves the wettability of the starting material, i.e., platinum dihalide complex, and lowers the freezing point of the solvent, which allows for a lower final temperature for product isolation and enhanced yield. Third, treatment of the reaction mixture with an adsorbent, such as decolorizing and flocculating agent (preferably activated carbon), to remove minor colored impurities and other undissolved components prior to product crystallization allows for the removal of insoluble excess sodium pyrophosphate prior to product isolation and hence eliminates the upper concentration limit on the reaction due to the precipitation of unreacted sodium pyrophosphate; in contrast, in the literature method the reaction concentration was limited by the potential precipitation of the unreacted sodium pyrophosphate reagent. Fourth, cooling the reaction mixture prior to pH adjustment for crystallization prevents product decomposition. Moreover, use of a more concentrated acid (2N versus 1N nitric acid) to adjust pH for product precipitation allows for faster acid addition and reduces dilution of the reaction mixture during product precipitation step, and hence reduces loss of product to the filtration mother liquor. Finally, the present invention has demonstrated that monomeric amine or diamine platinum pyrophosphate compounds can be prepared in a "one-pot" or "one-drop" process in high quality and good yield without further purification steps.

The term "water-miscible organic solvent", as used herein, refers to an organic solvent that is completely miscible with water at room temperature. Examples of water-miscible organic solvents are well known to a person of ordinary skill in the art. They include, but are not limited to lower alkyl alcohols, lower alkyl diols (e.g., ethylene glycol, 1,3-propanediol, etc.), ketones (acetone, 2-butanone, etc.), acetonitrile, tetrohydrofuran, acetic acid, or the like.

The term "lower alkyl alcohol", as used herein, refers to an aliphatic alcohol having one to eight, preferably one to six, and more preferably one to four, carbon atoms, including but not limited to methanol, ethanol, 1-propanol, 2-propanol (isopropanol), n-butanol, iso-butanol, tert-butanol, or the like.

The term "precipitating", "crystallizing", or the like, as used herein, refers to step in which a solid, preferably a desired product, precipitates out from a solution upon change of a condition or conditions, such as concentrations, pH, and/or temperature. As would be understood by a person skilled in the art, when a product precipitates out as a crystalline solid, the term "precipitating" has essentially the same meaning as the term "crystallizing". Therefore, the two terms are sometimes interchangeable.

The term "high purity", "high quality", or the like, as used herein, means that a product has a purity of at least 96.0% (w/w), preferably at least 98.0% (w/w), more preferably at least 99.0% (w/w), and most preferably 99.5% (w/w) as assayed by HPLC in comparison with a reference standard of known purity. The purity of such a reference standard is preferably at least 99.0% (w/w), more preferably at least 99.5% (w/w), and most preferably at least 99.9% (w/w). It is within the knowledge and technique of a person of ordinary skill in the art to prepare such a reference standard (for example by multiple recrystallizations), to determine its purity by using various analytical instruments and methods, and to determine purity of a given product by comparing the product with the reference standard using a validated method, for example, HPLC assay.

When the term "about" is applied to a parameter, such as pH and temperature, it indicates that the parameter can vary by ±10%, preferably within ±5%. For example, a pH of "about 2" should be interpreted as falling into the range of 1.8 to 2.2, preferably 1.9 to 2.1. When the term "about" is applied to a purity data expressed as a percentage, it should be interpreted to follow the accepted convention of rounding and scientific significant figures. For example, a purity expressed at 96% implies that it encompasses a purity range of any sample greater than or equal to a purity of 95.5% and less than or equal to a purity of 96.49%. As would be understood by a person skilled in the art, when a parameter is not critical, a number is often given only for illustration purpose, instead of being limiting.

The term "a," "an," or "the," as used herein, represents both singular and plural forms. In general, when either a singular or a plural form of a noun is used, it denotes both singular and plural forms of the noun.

The Comparative Literature Processes and Conditions

In the reported synthesis of cis-1,2-cyclohexanediamine-(pyrophosphato) platinum(II) ("cis-dach-2"), for example, 250 mL water was used as solvent for the reaction using cis-1,2-cyclohexanediamine-dichloro-platinum(II) (0.100 g, 0.26 mmol) as the starting material to react with sodium pyrophosphate decahydrate (0.400 g). About 98% of the solvent needed to be evaporated at 48° C. under vacuum, followed by acidification with nitric acid to precipitate out the product.

Figure 2:
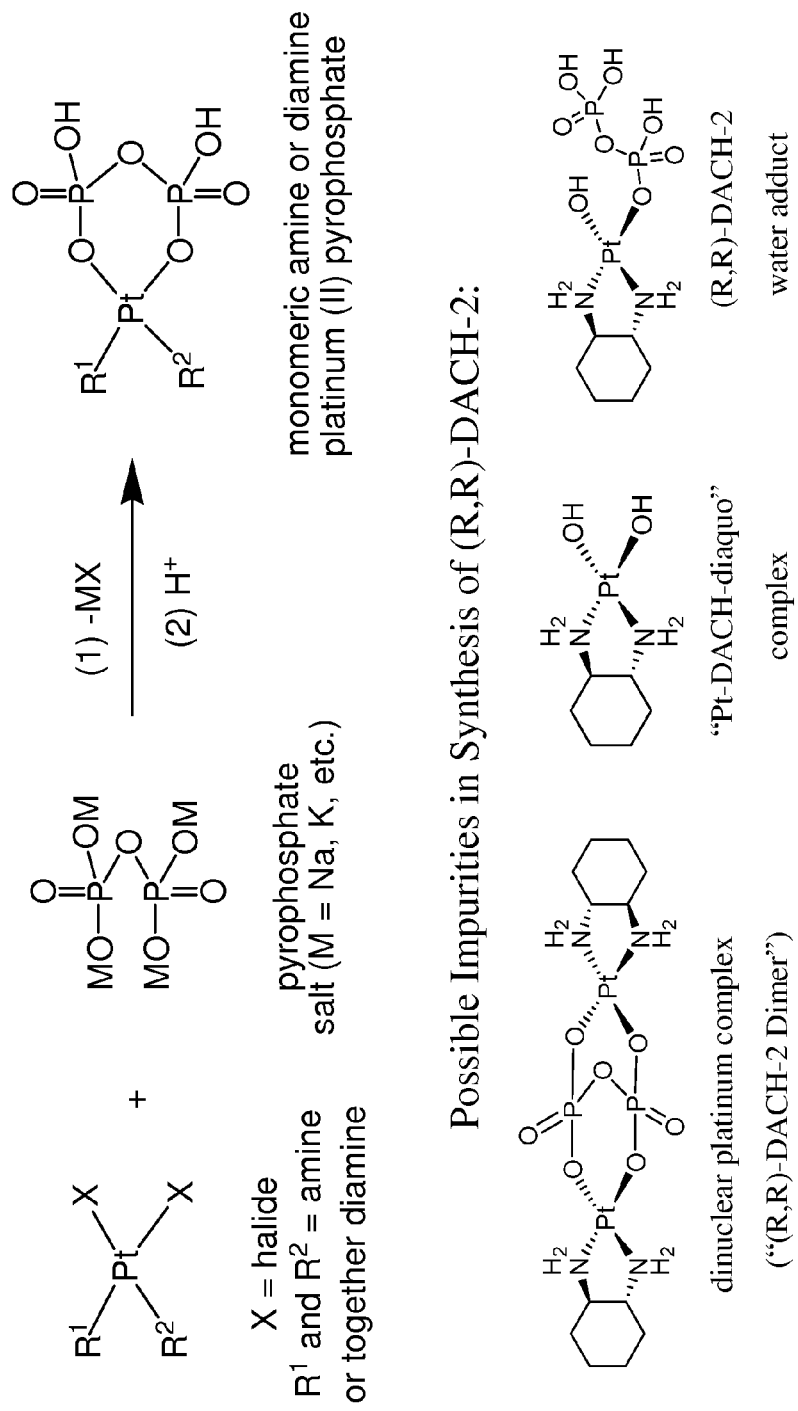
FIG. 2 illustrates a general synthetic scheme of monomeric amine or diamine platinum (II) pyrophosphate complexes and the structures of several possible impurities formed during the reaction in the synthesis of (R,R)-DACH-2.

Until the present invention disclosed herein, the most successful syntheses of monomeric diamine platinum pyrophosphate complexes are those reported by Bose, e.g., in WO 2011/153365A1, which is hereby incorporated by reference. A general synthetic scheme and the structures of several possible impurities in synthesis of (R,R)-DACH-2 are described in FIG. 2. Bose discloses synthesis of dach-2 by reaction of (1,2-cyclohexanediamine)-dichloroplatinum with excess sodium pyrophosphate at a temperature in the range from about 35° C. to about 45° C. and at a pH in the range from about 6 to about 9. Using the reported method, the present inventors have only been able to obtain the intended product in about 96.3% purity (HPLC area), with a yield of only between about 6.3% and 29.8%, resulting in a green-colored solid, which coloration indicates the presence of impurities. These experiments highlight the problems with this approach for investigative or commercial purposes, and the need for the further improvements disclosed herein.

The aqueous reaction mixture was concentrated to such an extent that precipitates of pyrophosphate do not form. Then, the pH of the reaction mixture was lowered rapidly to less than 2 by addition of an acid, such as 1N nitric acid, from which, followed by cooling, precipitates of the desired platinum pyrophosphate complexes were obtained.

Therefore, the literature method highlights, among others, the following critical conditions: (1) use of water as the reaction and crystallization solvent, (2) dilute reaction, (3) removal of most solvent (water) under reduced pressure prior to precipitation, and (4) rapid acidification of the concentrated reaction mixture for precipitation of the product. Even under optimized conditions, the existing methods afford the desired product in inconsistent yield and quality. So far as reported, the platinum pyrophosphate complexes have been prepared in only mM scales, e.g., 0.263 mM scale starting with 0.1 gm of DACH-Pt—$Cl_2$, and the yield has not been satisfactory for common applications of the compounds in pre-clinical or clinical investigation.

In an effort to prepare multi-gram quantities of (R,R)-DACH-2, the experimental protocol in *Inorg. Chem.*, 47, 7972 (2008) for synthesis of racemic DACH-2 was scaled up by a factor of 8× to starting with 0.8 gm of DACH-Pt—$Cl_2$. The protocol was repeated in duplicate (Example 2). The starting material trans-(1R,2R)DACH-Pt—$Cl_2$ (i.e. referred to as DACH-Pt—$Cl_2$ in the remainder of this document) was synthesized according to Example 1.

Simple scale-up of the original literature route for synthesis of the racemic analog to the synthesis of (R,R)-DACH-2 by a factor of 8 highlighted several problems that make the protocol unacceptable for scale-up to the manufacture of tens of grams of product, much less of 10s to 100s of kilograms of product. For example, first the reaction is extremely dilute. It would require an initial reaction volume of 78,349 L, (20,697 gallons) to prepare 10 kg product according to theoretical yield. Second, product isolation requires removal of most (98%) of the initial solvent by reduced-pressure distillation—an extremely energy intensive and time-consuming process. Third, the reaction gives only a low yield of the product. Moreover, the isolated product is often contaminated by undesirable Pt-containing by-products.

The present inventors discovered, among other things, that the synthesis of platinum pyrophosphate complexes can be conducted beneficially at much higher concentrations.

Reactions at Higher Concentrations

The literature suggested that the synthesis would need to be conducted in a homogenous solution in order to minimize undesired side reactions. In particular because it was believed that the starting material must be fully dissolved, the reactions were all conducted under extremely dilute conditions previously.

Simply increasing the reaction concentration described previously by a factor of 45- to 50-fold results in the initial presence of a large amount of undissolved starting material, DACH-Pt—$Cl_2$. This material wets poorly resulting in very poor mixing and, thus, inconsistent reaction and yield. The present inventors have now discovered that these issues can be addressed by adding a water miscible solvent to serve as a wetting agent. Water miscible alcohols are preferable and methanol was selected as most preferable based on the solubility of (R,R)-DACH-2 in various solvents including alcohols (Table 1). Addition of alcohols decreases the freezing point of water and hence allows one to conduct the reaction at lower temperatures than in water alone as solvent. Increasing the initial reaction concentration by a factor of 45-50 fold completely eliminates the need to concentrate the reaction mixture prior to product isolation. The present invention thus eliminates all of the problems associated with the earlier synthetic processes and allows for the reproducible synthesis of (R,R)-DACH-2 in a much more efficient and economical manner. The new method is suitable for the large-scale manufacture of the compound and can afford product in high yield and quality. Most significantly, the new method obviates the need to concentrate the reaction mixture by removal of approximately 98% of the solvent that was previously distilled prior to product isolation.

The inventors of the present invention have also found that, in some embodiments, it is more beneficial to add all the starting material DACH-Pt—$Cl_2$ in one portion at the start of the reaction than to add it in portions over time (as illustrated in a comparison between Examples 3 and 4). Therefore, the present inventors have surprisingly discovered that the reaction at a high concentration of DACH-Pt—$Cl_2$ produced the desired product in higher yield and quality, contrary to the conventional belief. The reaction rate is a function of reaction concentration, reaction temperature and sodium pyrophosphate stoichiometry. While Example 5 shows that good yields can be achieved with only a 2-fold excess of tetrasodium pyrophosphate, preferably faster reaction times are achieved with a 3.2-fold excess (Example 6 and 7).

The examples provided are by no means comprehensive, but simply illustrate the effect of stoichiometry and reaction temperature on the overall rate of the reaction. Therefore, similar reactions using less tetrasodium pyrophosphate, for example, only 1 mole equivalent, are encompassed by the present invention.

Measurement of the Product Solubility

To help understand the effect of the discovery, the solubility of (R,R)-DACH-2 in various organic solvents was measured gravimetrically. To this end, 200 mg of (R,R)-DACH-2 was suspended in 5 ml of pure solvent, stirred at ambient temperature for 30 min followed by heating to 40° C. and stirring for 30 min. The suspension was filtered, dried in vacuo at 40° C., and the solubility of (R,R)-DACH-2 at 40° C. determined from the weight of recovered material.

TABLE 1

Solubility data of (R,R)-DACH-2 at 40° C.

| Solvent | Solubility (mg/ml) |
| --- | --- |
| methanol | 1.4 |
| tetrahydrofuran | 2.0 |
| dioxane | 2.8 |
| tert-butylmethylether | 3.2 |
| ethanol | 3.4 |
| ethylacetate | 3.6 |
| 1-butanol | 4.0 |
| dichloromethane | 4.2 |
| isopropylacetate | 4.8 |
| chloroform | 5.0 |
| toluene | 5.2 |
| cyclohexane | 5.4 |
| acetone | 5.6 |
| pentane | 6.6 |
| heptane | 6.8 |
| dimethylformamide | 7.4 |
| isopropanol | 7.8 |

Controlling Precipitation of Unreacted Pyrophosphate Salts

The literature specifically suggests that concentration of the reaction mixture prior to product isolation must be conducted in a manner to avoid precipitates of pyrophosphate. Under the reaction conditions disclosed herein, controlling precipitation of unreacted pyrophosphates is completely unnecessary as exemplified by Examples 8 and 9. Thus, the concern over pyrophosphate precipitates does not place a limitation on the upper end of the reaction concentration as suggested in the literature.

Use of a Decolorizing Agent

Under both of the reaction conditions of this process, and particularly under the reaction conditions of the literature, colored impurities are formed in the reaction. Failure to remove these impurities prior to product isolation results in isolation of product containing a greenish cast to a full green color in contrast to the desired off-white to pale yellow color of the pure compound. Treating the reaction mixture with a decolorizing agent, such as activated carbon, was discovered to eliminate color. (see, e.g., Examples 5, 6, and 9). In addition, it was discovered that the decolorizing agent can also serve as a flocculating agent that facilitates removal of any fines or of any unreacted pyrophosphate precipitates by filtration prior to product isolation.

(R,R)-DACH-2 Solution Stability Study

Studies were conducted to measure the stability of a saturated aqueous solution of (R,R)-DACH-2 at pH 2 as summarized in Example 10. This data shows that (R,R)-DACH-2 readily suffers hydrolytic degradation in aqueous solution at pH 2. The degradation rate is significantly reduced as temperature is reduced. Thus, the data indicate that it is highly desirable to conduct the process of pH adjustment, for product precipitation from the synthetic reaction, at as low a temperature as possible. Reaction in a mixed aqueous organic solvent system, particularly an alcohol, decreases the freezing point of the reaction solvent and provides for a lower reaction temperature than a reaction in pure water.

Recrystallization and Purification of (R,R)-DACH-2 Complex

In another aspect, the present invention provides a process for recrystallization and purification of (R,R)-DACH-2. The process involves dissolution in a buffer system, such as sodium bicarbonate or sodium nitrate buffer, or other buffer systems containing a hard anion, at pH between about 6 to about 9. Preferably tetrasodium pyrophosphate is also present in the buffer system. The reaction mixture may be heated to facilitate dissolution. The stirred solution is treated with a decolorizing agent such as activated carbon, filtered, cooled to approx 0° C. and the pH adjusted to 2 with nitric acid. The resultant precipitate is collected, washed with water and methanol, and dried. The wash solvents may optionally be pre-chilled. This process is particularly effective in removing the impurities including DACH-Pt—$Cl_2$, the dimeric decomposition product of (R,R)-DACH-2 formed at low pH, and pyrophosphate impurities. The new recrystallization and purification method can readily provide isolated monomeric platinum pyrophosphate compounds in greater than 97% purity, preferably greater than 98% purity, and more preferably greater than 99% purity as measured by HPLC. Therefore, in one aspect, the present invention encompasses these high purity complexes and methods of preparing them.

The present invention is described more fully by way of the following non-limiting examples. The following examples illustrate the process, and modifications of these examples will be apparent to those skilled in the art.

EXAMPLES

A. HPLC Analytical Method for Determining the Assay and Related Substances of (R,R)-DACH-2

Instrument: Waters Acquity uPLC H-Class or equivalent
Column: uPLC Column High Strength Silica (HSS)$C_{18}$ Waters, 2.1×50 mm, 1.8 pm
Detector Wavelength: UV, 205 nm (Assay: 210 nm)
Mobile Phases: A: 0.1% Trifluoroacetic acid
B: Acetonitrile
Gradient profile:

| Step | Time (min) | Flow [mL] | A [%] | B [%] |
|---|---|---|---|---|
| 1 | Initial | 0.500 | 100.0 | 0 |
| 2 | 1.50 | 0.500 | 100.0 | 0 |
| 3 | 4.50 | 0.500 | 90.0 | 10.0 |
| 4 | 4.60 | 0.500 | 100.0 | 0 |
| 5 | 6.50 | 0.500 | 100.0 | 0 |

Injection volume: 2.2 µL (Assay 0.4 µL)
Limit of Detection (LOD) 0.03%; Limit of Quantification (LOQ) 0.09%
Sample preparation: Dissolve 32 mg of sample in 10 mL of the diluent solution
Approximate Retention Times of Main Peaks:

| Analyte | Approx. RT [min] |
|---|---|
| (R,R)-DACH-2 water adduct | 0.6-0.7 |
| (R,R)-DACH-2 | 0.7-0.8 |
| Pt-DACH-$Cl_2$ | 1.2 |
| Pt-DACH-diaquo | 1.5 |
| (R,R)-DACH-2 Dimer | 4.9 |

Diluent Preparation: In a 1000-ml volumetric flask dissolve 1.583 g ammonium hydrogen carbonate with deionized water. Dilute to standard and mix well.
(R,R)-DACH-2 Standard Preparation: Add 32 mg of (R,R)-DACH-2 standard to a 10-ml volumetric flask, dissolve and dilute to standard with ammonium hydrogencarbonate diluent.
Pt-DACH-$Cl_2$ Standard Preparation: Add 5 mg Pt-DACH-$Cl_2$ to a 50-ml volumetric flask, dissolve and dilute with 0.9% sodium chloride solution. Transfer 5 mL of this solution immediately after preparation to a 50-ml-volumetric flask and make up to volume with 0.9% sodium chloride solution. Mix well.

B. Analytical Method for Determining Anionic Impurities in (R,R)-DACH-2

Instrument: Dionex ion chromatograph model ICS 2100 or equivalent
Column: Doinex AS 11, 250×4.0 mm
Flow: 1.0 mL/min
Detection: Conductivity
Mobile Phase Linear Gradient with aqueous KOH-solution
Injection Volume: 20 µL
Sample preparation: 2 mg/ml in 20 mM aqueous sodium bicarbonate

| Time [min.] | Conc. KOH [mMol/L] |
|---|---|
| 0 | 5.00 |
| 15 | 40.00 |
| 20 | 40.00 |
| 23 | 5.00 |

Example 1

Synthesis of trans-(1R,2R)-DACH-Pt—$Cl_2$

Potassium tetrachloroplatinate (85.0 gm 0.02 mole) was dissolved in 633 ml of deionized water and filtered. To the resulting red solution was added a solution of trans-(1R,2R)-cyclohexyldiamine (28.0 gm 0.24 mole) dissolved in 126 ml of deionized water. The resulting reaction mixture was stirred for 66 hours at 20° C. during which time a yellow precipitate formed. The suspension was filtered and the solids washed sequentially with deionized water (500 ml) and methanol (402 gm), followed by vacuum drying at 40° C./25 mbar, to afford 71.11 gm (91.3%) yield of a yellow solid, trans-(1R,2R)-DACH-Pt—$Cl_2$. HPLC purity; 98.8% area.

Example 2

Synthesis of (R,R)-DACH-2 (repeating Bose method at an 8× scale)

Trans-(1R,2R)-DACH-Pt—$Cl_2$ (0.8 gm, 1.649 mmole) was added to a solution of tetrasodium pyrophosphate decahydrate (3.2 gm, 7.10 mmole) in 1981 ml of deionized water. The solution was adjusted to pH 8 with 2 N nitric acid (approx. 0.08 gm), heated to 40° C. and stirred for 15 hours during which time the pH decreased to about 6.6. The reaction mixture was concentrated to a residual volume of 40 ml by reduced pressure evaporation. The pH of the concentrate was 5.7. The stirred solution, immersed in an ice bath, was adjusted to pH 2 with 2 N nitric acid (approx. 1 gm). A precipitate slowly formed which was isolated by filtration and washed sequentially with cold deionized water (79 ml) and acetone (63 gm). Vacuum drying afforded a greenish solid. The first experiment afforded 0.13 gm (6.3%), while the second afforded 0.30 gm (29.8%) product. The latter sample showed a single $^{31}P$ NMR resonance at +1.51 ppm (bicarbonate $D_2O$ pH unknown) [Literature (Inorg. Chem. 47, 7972 (2008)) for racemic (R,R)-DACH-2, +1.78 ppm (~100 mM in $D_2O$, pH 7.93)], and a single $^{195}Pt$ NMR resonance a –1755 ppm, [Literature (Inorg. Chem. 47, 7972 (2008)) for racemic (R,R)-DACH-2, –1729 ppm (~100 mM in $D_2O$, pH 7.93)]. HPLC purity 96.3% area, purity by gravimetric platinum determination, 97%.

Example 3

Portion-wise Addition of DACH-Pt—$Cl_2$

Tetrasodium pyrophosphate decahydrate (20.5 gm 46 mmole) was dissolved in 250 ml of deionized water. The mixture was adjusted to pH 8 with 2 N nitric acid (3-5 ml). The solution was heated to 40° C. and DACH-Pt—$Cl_2$ (5.0 gm, 13.1 mmole) was added in 5×1 gm portions over an 8 hr period. The resulting suspension was stirred for an additional 15 hr at 40° C. during which time all of the solids did not dissolve. The reaction mixture was increased to 60° C. and stirring was continued for an additional 22 hour during which time all of the solids had dissolved to afford a clear greenish colored solution. The solution was cooled to ambient temperature and the pH adjusted to 2 with 2 N nitric acid (30-35 ml). On further cooling to 5° C. a precipitate formed. The green solid was collected by filtration, and sequentially washed with deionized water (3×15 ml) and methanol (3×15 ml). Vacuum drying afforded 2.6 gm (40.9% yield) of a greenish colored solid. A second crop of solids was collected from the filtrate. HPLC analysis showed both solids contained approx 75% unreacted starting material and only a low yield of (R,R)-DACH-2.

Example 4

Addition of the DACH-Pt—$Cl_2$ in One Portion

DACH-Pt—$Cl_2$ (5.0 gm 13.1 mmole) was added as a single portion to a solution of tetrasodium pyrophosphate decahydrate (20.5 gm 46 mmole) dissolved in 250 ml of deionized water and 10 ml methanol. The mixture was adjusted to pH 8 with 2 N nitric acid (3-5 ml), heated to 60° C. and stirred for 15 hours, during which time all of the solids dissolved to afford a clear greenish colored solution. The reaction mixture was cooled to ambient temperature, and 2 gm of activated carbon was added. After stifling for several minutes the carbon was removed by filtration to afford a clear colorless solution. The solution was adjusted to pH 2 with 2 N nitric acid (30-35 ml) and cooled to 5° C. where a precipitate formed. The solid was isolated by filtration, and washed sequentially with deionized water (3×15 ml) and methanol (3×15 ml) and dried under vacuum to afford an off-white solid (4.8 gm, 75.5% yield). HPLC analysis results: 97.6% (area) (R,R)-DACH-2, 2.3% (area) DACH-Pt—$Cl_2$, and 0.1% (area) unknown impurities.

Example 5

Synthesis of (R,R)-DACH-2 with 2.0 eq. Pyrophosphate

DACH-Pt—$Cl_2$ (5.0 gm 13.1 mmole) was added as a single portion to a solution of tetrasodium pyrophosphate decahydrate (11.7 gm 26.3 mmole) dissolved in 250 ml of deionized water and 10 ml methanol. The mixture was adjusted to pH 8 with 2 N nitric acid (3-5 ml), heated to 60° C. and stirred for 48 hours to afford a turbid greenish colored solution. Activated carbon (2 gm) was added and stirring at 60° C. continued for 1 hour. The solution was filtered and cooled to ambient temperature where the pH was adjusted to 2 with 2 N nitric acid (30-35 ml). The mixture was cooled to 5° C. and the resultant precipitates collected by filtration. The solids were sequentially washed with deionized water (3×15 ml) and methanol (3×15 ml). Vacuum drying afforded 3.6 gm (56% yield) of a very slightly greenish colored solid. HPLC analysis: 97.5% (area) (R,R)-DACH-2, 1.07% (wt/wt) DACH-Pt—$Cl_2$, and 0.1% (area) unknown impurities.

Example 6

Synthesis of (R,R)-DACH-2 with 3.2 eq. Pyrophosphate ($H_2O$:MeOH=25:1 v/v)

Tetrasodium pyrophosphate decahydrate (59.8 gm 134.14 mmole) was dissolved in a mixture of deionized water (750 ml) and methanol (30 ml). The pH of the mixture was adjusted to 8 with 2 N nitric acid. DACH-Pt—$Cl_2$ (15.0 gm 39.45 mmole) was added as a single portion and the resulting mixture heated to 60° C. Stirring was continued for 26 hours, during which time all of the solids dissolved to afford a clear colorless solution. The solution was cooled to ambient temperature and activated carbon (1.2 gm) added. The resultant mixture was stirred for 65 hours at ambient temperature. The solution was filtered and adjusted to pH 2 with 2 N nitric acid resulting in formation of a precipitate. The slurry was cooled to 5° C., stirred for several minutes and the solids isolated by filtration. The filter cake was washed sequentially with deionized water (3×40 ml) and methanol (3×40 ml). After vacuum drying 17.1 gm (89.7% yield) of solid product was isolated. HPLC analysis results: 95.5% (area) (R,R)-DACH-2, 2.0% (wt/wt) DACH-Pt—$Cl_2$, 0.4% (area) unknown impurities.

Ion Chromatography analysis results: 1.19% (wt/wt) $P_2O_7^{2-}$, 0.1% (wt/wt) Cl⁻, 0.01% (wt/wt) $PO_4^{3-}$.

Example 7

Synthesis of (R,R)-DACH-2 with 3.2 eq. Pyrophosphate ($H_2O$:MeOH=7:3 v/v)

Tetrasodium pyrophosphate decahydrate (59.8 gm 134.14 mmole) was dissolved in a mixture of deionized water (525 ml) and methanol (225 ml). The pH of the mixture was adjusted to 8 with 2 N nitric acid. DACH-Pt—$Cl_2$ (15.0 gm 39.45 mmole) was added as a single portion and the resulting mixture heated to 60° C. After stifling for 16 hours a colorless turbid solution was obtained. The solution was cooled to ambient temperature and adjusted to pH 2 with 2 N nitric acid, resulting in formation of a precipitate. The slurry was cooled to 5° C. and stirred for several minutes during which time the solids increased. After stirring for several minutes, the solids were isolated by filtration and washed sequentially with deionized water (3×40 ml) and methanol (3×40 ml). Vacuum drying afforded an off white to yellow solid (16.5 gm, 86.1% yield). HPLC analysis: 95.3% (area) (R,R)-DACH-2, 1.9% (wt/wt) DACH-Pt—$Cl_2$, and 0.1% (area) unknown impurities. Ion Chromatography analysis: 0.87% (wt/wt) $P_2O_7^{2-}$, 0.05% (wt/wt) Cl⁻, 0.12% (wt/wt) $NO_3^-$, and 0.04% (wt/wt) $PO_4^{3-}$.

Example 8

Effect of Controlling Precipitation of Unreacted Pyrophosphate (Without Decolorizing Agent, cf. Example 9)

Tetrasodium pyrophosphate decahydrate (151.6 gm 339.83 mmole) was added to 1330 ml of deionized water, and the resultant mixture heated to 60° C. The resulting solution was adjusted to pH 8 with 2 N nitric acid followed by the addition of methanol (500 ml). DACH-Pt—$Cl_2$ (38.0 gm 99.95 mmole) was added as a single portion and the resulting mixture was stirred for 40 hours at 60° C., affording an almost clear solution. After cooling to 1° C. the pH was adjusted with 2 N nitric acid and stifled. When pH 2 was reached a precipitate formed after 1-2 minutes. After stifling for an additional 5 minutes the precipitate was collected by filtration and sequentially washed with deionized water (3×40 ml) and methanol (3×40 ml). Vacuum drying afforded 44.79 gm (81.2% yield) of a slightly yellow colored solid. HPLC analysis: 87.6% (wt/wt) (R,R)-DACH-2, 0.14% (wt/wt) DACH-Pt—$Cl_2$, 0.05% (area) unknown impurities, and 0.1% (area) (R,R)-DACH-2 dimer. Ion Chromatography analysis: 15% (wt/wt) $P_2O_7^{2-}$, 0.01% (wt/wt) Cl⁻, 0.02% (wt/wt) $NO_3^-$, and 0.04% (wt/wt) $PO_4^{3-}$.

Example 9

Effect of Controlling Precipitation of Unreacted Pyrophosphate (With Decolorizing Agent)

Tetrasodium pyrophosphate decahydrate (75.8 gm 169.92 mmole) was added to 665 ml of deionized water, and the resultant mixture heated to 60° C. The resulting solution was adjusted to pH 8 with 2 N nitric acid followed by the addition of methanol (360 ml). DACH-Pt—$Cl_2$ (19.0 gm 49.98 mmole) was added as a single portion and the resulting mixture was stirred for 88 hours at 60° C. affording white suspension. Activated carbon (1.5 gm) was added at 60° C., and the solution stirred and filtered. The pale yellow filtrate was cooled to 2° C. and the pH adjusted with 2 N nitric acid. Within 1-2 minutes a precipitate formed, the slurry was stirred for an additional 5 minutes. The precipitate was collected by filtration and sequentially washed with deionized water (3×40 ml) and methanol (3×40 ml). Vacuum drying afforded 19.21 gm (79.5% yield) of a slightly yellow colored solid in such purity levels that no recrystallization or purification steps may be necessary. HPLC analysis: 102.2% (wt/wt) (R,R)-DACH-2, 0.02% (wt/wt) DACH-Pt—$Cl_2$, 0.02% (area) unknown impurity, and 0.05% (area) (R,R)-DACH-2 dimer. Ion Chromatography analysis: 0.25% (wt/wt) $P_2O_7^{2-}$, 0.01% (wt/wt) Cl⁻, <0.01% (wt/wt) $NO_3^-$, and 0.01% (wt/wt) $PO_4^{3-}$.

Example 10

Stability of Saturated Aqueous Solutions of (R,R)-DACH-2 at pH 2

A saturated aqueous solution of (R,R)-DACH-2 at pH 2 was prepared by adding 300 mg of (R,R)-DACH-2 to 15 ml of deionized water. The resultant suspension was stirred for 30 min and the pH adjusted to 2 with 0.1M nitric acid. The solution was filtered through a 0.45 micron Whatman polypropylene filter to afford a clear solution. Samples of the solution were stored at 25° C. and 5° C. At the time intervals shown in Tables 2 and 3 the solution composition was determined by HPLC.

TABLE 2

Stability of (R,R)-DACH-2 in aqueous solution at pH 2 and 25° C.

| | | HPLC Area % | | | |
|---|---|---|---|---|---|
| Time (h) | (R,R)-DACH-2 concentration (mg/ml) | (R,R-DACH-2 water adduct | (R,R)-DACH-2 | Pt-DACH-diaquo | (R,R)-DACH-2 dimer |
| 0.1 | 2.38 | 13.3 | 67.1 | 16.7 | 2.9 |
| 2 | 1.75 | 9.3 | 50.6 | 25.8 | 14.3 |
| 4 | 1.59 | 9.2 | 48.7 | 24.8 | 17.4 |
| 8 | 1.41 | 9.5 | 51.6 | 25.5 | 13.4 |
| 16 | 1.04 | 9.8 | 56.5 | 25.6 | 8.1 |
| 24 | 0.88 | 10.1 | 57.6 | 25.3 | 7 |
| 48 | 0.62 | 9.3 | 59.5 | 25.9 | 5.5 |

TABLE 3

Stability of (R,R)-DACH-2 in aqueous solution at pH 2 and 5° C.

| | | HPLC Area % | | | |
|---|---|---|---|---|---|
| Time (h) | (R,R)-DACH-2 concentration (mg/ml) | (R,R-DACH-2 water adduct | (R,R)-DACH-2 | Pt-DACH-diaquo | (R,R)-DACH-2 Dimer |
| 0.1 | 0.1 | 2.5 | 12.8 | 68.3 | 16.8 |
| 2 | 2 | 2.22 | 11.7 | 60.9 | 24.2 |
| 4 | 4 | 2.02 | 10.6 | 57.2 | 29.2 |
| 8 | 8 | 1.81 | 9.6 | 53.6 | 33.5 |
| 16 | 16 | 1.63 | 9.3 | 52.5 | 35.1 |
| 24 | 24 | 1.43 | 9.4 | 51.5 | 36.2 |
| 48 | 48 | 1.27 | 9.3 | 53.8 | 34.7 |

Example 11

Recrystallization and Purification of (R,R)-DACH-2 Complex

Tetrasodium pyrophosphate decahydrate (7.31 gm 16.39 mmole) was dissolved in 168 ml of deionized water. The solution was heated to 60° C., and (R,R)-DACH-2 (3.364 gm 6.93 mmole) was added along with sufficient sodium bicarbonate to adjust the pH to 8. All of the solids dissolved after approximately 10 minutes of stirling. Activated carbon 8% (wt/wt), relative to the (R,R)-DACH-2 (0.269 gm), was added and the mixture was stirred for 30 minutes. The solution was filtered and cooled to 0° C. where the pH was adjusted to 2 with 2 N nitric acid. A precipitate formed after approximately 10 minutes of stirring. After an additional 15 minutes of stirring, the slurry was filtered and the solids washed sequentially with deionized water (3×25 ml) and methanol (3×25 ml) followed by vacuum drying. Yield 1.651 gm (49.1%), and analytical data shown in Table 4.

TABLE 4

Analytical data on recrystallized (R,R)-DACH-2

|  | Recrystallized product |
| --- | --- |
| (R,R)-DACH-2 | 98.7% (wt/wt) |
| DACH-Pt-Cl$_2$ | <0.01% (wt/wt) |
| Unknown | 0.04% (area) |
| (R,R)-DACH-2 Dimer | 0.08% (area) |
| pyrophosphate | 0.11% (wt/wt) |
| chloride | 0.02% (wt/wt) |
| nitrate | 0.01% (wt/wt) |
| phosphate | 0.01% (wt/wt) |

Example 12

Recrystallization and Purification of (R,R)-DACH-2 Complex

Tetrasodium pyrophosphate decahydrate (7.25 gm 16.25 mmole) was dissolved in 95 ml of deionized water. The solution was heated to 60° C., and (R,R)-DACH-2 (3.335 gm 6.87 mmole) was added along with sufficient sodium bicarbonate to adjust the pH to 8. All of the solids dissolved after approximately 10 minutes of stirling. Activated carbon 8% (wt/wt), relative to the (R,R)-DACH-2 (0.267 gm) was added and the mixture was stirred for 30 minutes. The solution was filtered and cooled to 0° C. where the pH was adjusted to 2 with 2 N nitric acid. A precipitate formed after approximately 10 minutes of stirring. After an additional 15 minutes of stirring, the slurry was filtered and the solids washed sequentially with deionized water (3×27 ml) and methanol (3×27 ml) followed by vacuum drying. Yield 1.678 gm (50.3%), and analytical data shown in Table 5.

TABLE 5

Analytical data on recrystallized (R,R)-DACH-2

|  | Starting (R,R)-DACH-2 | Recrystallized product |
| --- | --- | --- |
| (R,R)-DACH-2 | 97.5% (area) | 99.5% (wt/wt) |
| DACH-Pt-Cl$_2$ | 1.07% (wt/wt) | not detected |
| Unknown | 0.1% (area) | not detected |
| (R,R)-DACH-2 Dimer | 0.02% (area) | 0.08% (area) |
| pyrophosphate | — | 0.08% (wt/wt) |
| chloride | — | 0.04% (wt/wt) |
| nitrate | — | 0.02% (wt/wt) |
| phosphate | — | <0.01% (wt/wt) |

Example 13

Recrystallization and Purification of (R,R)-DACH-2 Complex and Long-term Stability of the Recrystallized Product Tetrasodium pyrophosphate dehydrate (91.3 gm 204.68 mmole) was dissolved in 500 ml of deionized water and sufficient sodium bicarbonate was added to adjust the pH to 8. The buffer solution was heated to 60° C. and (R,R)-DACH-2 (43 gm 88.62 mmole) was added, resulting in complete dissolution of the solids. The pH was adjusted to pH 8 by the addition of small amounts of sodium bicarbonate. After stirling for approximately 10 minutes, activated carbon 8% (wt/wt) relative to the (R,R)-DACH-2 (3.5 gm) was added. The resulting mixture was stirred for 30 minutes at 60° C. The solution was filtered and cooled to 2° C. where the pH was adjusted to 2 with 2 N nitric acid. Within 1-2 minutes of reaching pH 2 a precipitate formed. The slurry was stirred for an additional 10 min after initial precipitate formation. The slurry was filtered and the solids washed sequentially with deionized water (3×300 ml) and methanol (3×300 ml) followed by vacuum drying. Yield 15.13 gm (35.2%), and analytical data shown in Table 6.

A long-term stability study of the recrystallized sample was conducted. After being stored in the original container (100 mL native HDPE bottle with a HDPE screw cap) at a temperature not exceeding 25° C. at a humidity of 60±5% for 14 months, the purity of the product changed only slightly, from 99.78% area and 99.4% w/w to 99.60% area and 98.4% w/w, while the contents of the (R,R)-DACH-2 dimer, Pt-DACH-diaquo, and unknown impurities changed from "not detected" to 0.18% area, 0.01% area, and 0.19% area, respectively (Table 6). These results show that the purified (R,R)-DACH-2 is stable.

TABLE 6

Analytical data of the (R,R)-DACH-2 product

|  | Starting (R,R)-DACH-2 | Recrystallized product | Re-testing after 14 months |
| --- | --- | --- | --- |
| (R,R)-DACH-2 | 99.71% (area) | 99.78% (area) | 99.60% (area) |
| (R,R)-DACH-2 | 87.6% (wt/wt) | 99.4% (wt/wt) | 98.4% (wt/wt) |
| DACH-Pt-Cl$_2$ | 0.14% (wt/wt) | not detected | not detected |
| Unknown | 0.05% (area) | not detected | 0.19% (area) |
| (R,R)-DACH-2 Dimer | 0.10% (area) | not detected | 0.18% (area) |
| Pt-DACH-diaquo |  | not detected | 0.01% (area) |
| pyrophosphate | 15% (wt/wt) | 0.17% (wt/wt) | 0.17% (wt/wt) |
| chloride | 0.01% (wt/wt) | 0.01% (wt/wt) | 0.01% (wt/wt) |
| nitrate | 0.02% (wt/wt) | 0.01% (wt/wt) | 0.01% (wt/wt) |

Example 14

Preparation of (R,R)-DACH-2 Reference Standard and Stability Study

Synthesis of Crude (R,R)-DACH-2

A solution of sodium pyrophosphate tetrahydrate (123.7 g, 277.23 mmol) in DI water (1085 mL) was prepared and heated to 60° C. The solution was adjusted to pH=8 with 2N nitric acid, and methanol (588 mL) was added. Pt-DACH-Cl$_2$ (31.0 g, 81.54 mmol) was added as a solid in one portion to the solution and stirred. After that period a white suspension with only little turbidity was obtained. Upon filtration, after cooling down to about 2° C., the slightly yellow filtrate was adjusted to pH=2 with 2N nitric acid and stirred. When pH 2 was reached, precipitates formed after one to two minutes, and the suspension was stirred for additional 5 minutes after the first appearance of turbidity. The precipitate was filtered off to yield the crude (R,R)-DACH-2 product (48.81 g) as slightly yellow solid. It was washed with water and methanol and dried in vacuum at 40° C. for 96 h. HPLC assay showed 99.62% (area) and about 67.5% (w/w) purity based on a working reference standard of 96.8% (w/w) purity. HPLC assay showed other impurities: Pt-DACH-Cl$_2$, 0.10% (area); (R,R)-DACH-2 dimer, 0.24% (area); and unknown impurities, 0.04% (area). The ion chromatography assay showed the content of $P_2O_7^2$ in about 34% (w/w), indicating that the product contained a substantial amount of unreacted sodium pyrophosphate.

Recrystallization of (R,R)-DACH-2

A buffer solution was prepared by dissolving sodium bicarbonate (18.8 g) and sodium pyrophosphate tetrahydrate (53 g) in DI water (914 mL) and adjusted to pH 8 under stifling. The buffer solution was heated to 60° C. The crude (R,R)-DACH-2 product (45.56 g, 67.5% w/w purity, containing 30.7 g of product by assay) was added and completely dissolved in the buffer solution after stifling for about 10 min. Activated carbon (0.64 g, 2% w/w based on the (R,R)-DACH-2 input) was added to the solution and filtered off after stifling for 15 min. The resultant filtrate was cooled to about 1° C. and adjusted to about pH 2. When pH 2 was reached, precipitates formed in one to two minutes, and the suspension was stirred for additional 10 minutes after the first appearance of turbidity. The precipitates were collected by filtration via a P5 glass frit. The solid was washed with cold DI water and methanol, and dried in vacuum, which gave (R,R)-DACH-2 (15.26 g, 49.6% recovery) in a purity of 99.8% (area) and 101.6% (w/w) as assayed against a working reference standard of 96.8% (w/w/) purity. HPLC assays showed the contents of other impurities: Pt-DACH-Cl$_2$, not detectable; (R,R)-DACH-2 "dimer", 0.15% (area); and Pt-DACH-diaquo, 0.03% (area); and the ion chromatography assay showed 0.10% (w/w) of pyrophosphate anion ($P_2O_7^{2-}$). The $^{13}C$ NMR spectrum of (R,R)-DACH-2 in aqueous sodium bicarbonate buffer at PH 7 shows three resonances at 23.56 ppm, 31.41 ppm 82.44, the latter is split due to Pt coupling, while the $^{112}Pt$ NMR spectrum shows a single resonance at 107 ppm. Differential scanning calorimetry (DSC) analysis showed a sharp exotherm followed by the large exotherm in the heat flow scan at 310° C., which is indicative of melting point of 310° C. with exothermic decomposition. Thermal gravimetric analysis of (R,R)-DACH-2 shows mass loss commencing around 310° C. consistent with sample decomposition on melting. For use as a reference standard the purity of the sample was assigned a purity of 99.35 (wt/wt) based on the standard method of subtracting the sum wt % of all the impurity from 100%.

Example 15

Scale-up Synthesis of (R,R)-DACH-Pt—Cl$_2$

Potassium tetrachloroplatinate K$_2$PtCl$_4$ (about 670.1 gm) was dissolved in purified water (about 5005 gm) and filtered. To the resulting red solution, a solution of R,R,-1,2-diaminocyclohexane (R,R-DACH) ligand was added at ambient temperature. The resulting mixture was stirred for 48 hours to form a yellow suspension. The yellow suspension was then filtered. The obtained solids were washed first with water (about 4020 gm) followed with acetone (about 3176 gm), and dried in vacuum at ambient temperature. (R,R)-DACH-Pt—Cl$_2$ was obtained in 93.2% yield (572.4 gm), with an HPLC purity of 96.4% (area).

Example 16

Scale-up of "One-Drop" Process for Synthesis of (R,R)-DACH-2

Sodium pyrophosphate decahydrate (1117 gm, 2504 mmole) was dissolved in purified water (9800 g) and heated to 60° C. under stifling. The pH of the resultant solution was adjusted to 8 with 2 N nitric acid. Methanol (4200 gm) was then added to the solution. DACH-Pt—Cl$_2$ (280 gm, 736 mmole) was added as solid in one portion to the solution, and the mixture was stirred for 88 hours. Activated carbon (22.40 gm) was then added to the resultant suspension at 60° C. After stirring for several minutes, the activated carbon and other solids were removed by filtration, and the filtrate solution was cooled down to about 2° C., and was then adjusted to about pH 2 with 2N nitric acid while stifling. Precipitates were obtained after stifling at about pH 2 for several minutes. The precipitates were collected by filtration, and the resultant yellow solid was washed with water and methanol, and then dried under vacuum at 40° C. to give (R,R)-DACH-2 in 80.7% yield (288.3 gm) with a 98.4% (w/w) purity as assayed by HPLC. Other assay results are shown in Table 7.

TABLE 7

| Analytical data of the (R,R)-DACH-2 product | |
|---|---|
| Parameter | Result |
| Assay HPLC (R,R)-DACH-2 [% w/w] | 98.4 |
| Impurities (by HPLC) | |
| Individual unknown impurity [% area] | 0.25 |
| Total unknown impurities [% area] | 0.38 |
| Pt-DACH-Cl2 [% w/w] | 0.38 |
| Pt-DACH-diaquo [% area] | 0.01 |
| (R,R)-DACH-2 Dimer [% area] | 0.33 |
| Impurities (by Ion Chromatography) | |
| $P_2O_7^{2-}$ [% w/w] | 0.13 |
| Cl$^-$ [% w/w] | 0.02 |
| $PO_4^{3-}$ [% w/w] | 0.02 |

The foregoing examples and description of the preferred embodiments should be interpreted as illustrating, rather than as limiting, the present invention as defined by the claims. It will be understood by those skilled in the art that numerous and various modifications can be made without departing from the spirit of the present invention.

What is claimed is:

1. A method of purifying a monomeric platinum pyrophosphate complex, or a salt thereof, comprising: dissolving the monomeric platinum pyrophosphate complex in a buffer; recrystallizing the complex from the buffer; isolating the monomeric platinum pyrophosphate complex; and washing and drying the isolated monomeric platinum pyrophosphate complex.

2. The method of claim 1, wherein the buffer is a bicarbonate buffer.

3. The method of claim 1, wherein said buffer has a pH in the range of about 6 to about 9.

4. The method of claim 1, wherein said dissolving comprises heating the monomeric platinum pyrophosphate complex in the buffer to an elevated temperature.

5. The method of claim 1, further comprising adding to the buffer solution of the monomeric platinum pyrophosphate complex a decolorizing agent, stirring for a period of time, and removing the decolorizing agent and any undissolved solids by filtration prior to said recrystallizing.

6. The method of claim 5, wherein the decolorizing agent is activated carbon.

7. The method of claim 1, further comprising passing the buffer solution of the monomeric platinum pyrophosphate complex through an inline filter comprising a filter medium to remove any undissolved solids to obtain a clear filtrate solution prior to said recrystallizing.

8. The method of claim 7, wherein said clear filtrate solution is transferred to another clean vessel for recrystallizing the product.

9. The method of claim 7, wherein said clear filtrate solution is circulated back to the vessel for dissolving the monomeric platinum pyrophosphate complex until all the buffer solution of the monomeric platinum pyrophosphate complex becomes clear.

10. The method of claim 7, wherein the filter medium comprises activated carbon.

11. The method of claim 1, wherein the buffer solution further comprises a pyrophosphate salt.

12. The method of claim 1, wherein the monomeric platinum pyrophosphate complex comprises two amine ligands independently selected from $NH_3$, substituted or unsubstituted aliphatic amines, and substituted or unsubstituted aromatic amines.

13. The method of claim 1, wherein the monomeric platinum pyrophosphate complex comprises an organic diamine ligand.

14. The method of claim 13, wherein said organic diamine is selected from substituted or unsubstituted aliphatic 1,2-diamines and substituted or unsubstituted aromatic 1,2-diamines.

15. The method of claim 13, wherein said organic diamine is an aliphatic 1,2-diamine selected from 1,2-ethylene-diamine and cyclohexane-1,2-diamine.

16. The method of claim 1, wherein the monomeric platinum pyrophosphate complex has a formula (I) or (II):

(I)

(II)

or a salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

17. The method of claim 16, wherein $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

18. The method of claim 16, wherein the platinum complex (II) is selected from:

and salts and mixtures thereof.

19. A method of preparing a monomeric platinum (IV) pyrophosphate complex, or a salt thereof comprising: (1) preparing a monomeric platinum (II) pyrophosphate complex according to the method of claim 16; (2) oxidizing the monomeric platinum (II) pyrophosphate complex prepared in (1) with hydrogen peroxide; and (3) isolating the monomeric platinum (IV) pyrophosphate complex.

20. The method of claim 19, wherein the monomeric platinum (IV) pyrophosphate complex has a formula (III) or (IV):

(III)

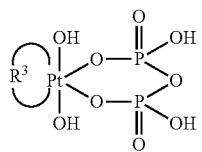 (IV)

or a salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic dimities.

21. The method of claim 20, wherein the monomeric platinum (IV) pyrophosphate complex has a formula (IV), wherein $R^3$ is 1,2-ethylene-diamine or cyclohexane-1,2-diamine.

* * * * *